(12) United States Patent
Kuriyama et al.

(10) Patent No.: US 11,025,835 B2
(45) Date of Patent: Jun. 1, 2021

(54) IMAGING DEVICE, ENDOSCOPE APPARATUS, AND METHOD FOR OPERATING IMAGING DEVICE

(71) Applicant: OLYMPUS CORPORATION, Tokyo (JP)

(72) Inventors: Naoya Kuriyama, Tokyo (JP); Koichiro Yoshino, Tokyo (JP); Satoshi Takekoshi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 271 days.

(21) Appl. No.: 15/963,263

(22) Filed: Apr. 26, 2018

(65) Prior Publication Data

US 2018/0249092 A1 Aug. 30, 2018

Related U.S. Application Data

(63) Continuation of application No. PCT/JP2015/080245, filed on Oct. 27, 2015.

(51) Int. Cl.
*H04N 5/262* (2006.01)
*A61B 1/00* (2006.01)
(Continued)

(52) U.S. Cl.
CPC ....... *H04N 5/2628* (2013.01); *A61B 1/00009* (2013.01); *A61B 1/00039* (2013.01); *A61B 1/00105* (2013.01); *A61B 1/00126* (2013.01); *A61B 1/00188* (2013.01); *A61B 1/313* (2013.01); *H04N 5/23212* (2013.01); *H04N 5/23245* (2013.01); *H04N 5/23293* (2013.01); *H04N 5/232123* (2018.08);

(Continued)

(58) Field of Classification Search
CPC .............. H04N 5/23212; H04N 5/2628; A61B 1/00188
See application file for complete search history.

(56) References Cited

U.S. PATENT DOCUMENTS

| 7,830,422 B2* | 11/2010 | Kaneda | H04N 5/23245 348/240.1 |
| 2005/0259161 A1* | 11/2005 | Lan | H04N 5/23293 348/224.1 |
| 2006/0104623 A1* | 5/2006 | Sasaki | H04N 5/23212 396/121 |

(Continued)

FOREIGN PATENT DOCUMENTS

| JP | S61-018271 A | 1/1986 |
| JP | 2007-279334 A | 10/2007 |

(Continued)

OTHER PUBLICATIONS

International Search Report dated Jan. 19, 2016 issued in PCT/JP2015/080245.

*Primary Examiner* — Boubacar Abdou Tchoussou
(74) *Attorney, Agent, or Firm* — Scully, Scott, Murphy & Presser, P.C.

(57) ABSTRACT

An imaging device includes a processor. The processor, in a manual focus mode, sets a focus evaluation area to have a larger size than the focus evaluation area set in an auto focus mode, generates assist information assisting adjustment of the in-focus object plane position based on a focus evaluation value obtained from an image of the focus evaluation area, and outputting the assist information to a display section.

5 Claims, 16 Drawing Sheets

(51) Int. Cl.
  *H04N 5/232*  (2006.01)
  *A61B 1/313*  (2006.01)
  *A61B 1/055*  (2006.01)
  *H04N 5/225*  (2006.01)

(52) U.S. Cl.
  CPC ........ *H04N 5/232945* (2018.08); *A61B 1/055* (2013.01); *H04N 2005/2255* (2013.01)

(56) References Cited

U.S. PATENT DOCUMENTS

| | | | |
|---|---|---|---|
| 2007/0229672 A1* | 10/2007 | Kaneda | H04N 5/23245 348/218.1 |
| 2008/0021271 A1* | 1/2008 | Pasero | A61B 1/00039 600/109 |
| 2009/0102960 A1 | 4/2009 | Tsuchiya | |
| 2009/0153649 A1* | 6/2009 | Hirooka | H04N 5/272 348/47 |
| 2013/0314579 A1* | 11/2013 | Sasaki | G02B 7/36 348/333.02 |
| 2014/0111628 A1 | 4/2014 | Yoshino et al. | |

FOREIGN PATENT DOCUMENTS

| | | |
|---|---|---|
| JP | 2008-216503 A | 9/2008 |
| JP | 2009-103912 A | 5/2009 |
| JP | 2009-142586 A | 7/2009 |
| JP | 2013-061618 A | 4/2013 |
| JP | 2014-078826 A | 5/2014 |
| JP | 2015-108670 A | 6/2015 |
| JP | 2015-118295 A | 6/2015 |
| WO | WO 2012/108294 A1 | 8/2012 |

\* cited by examiner

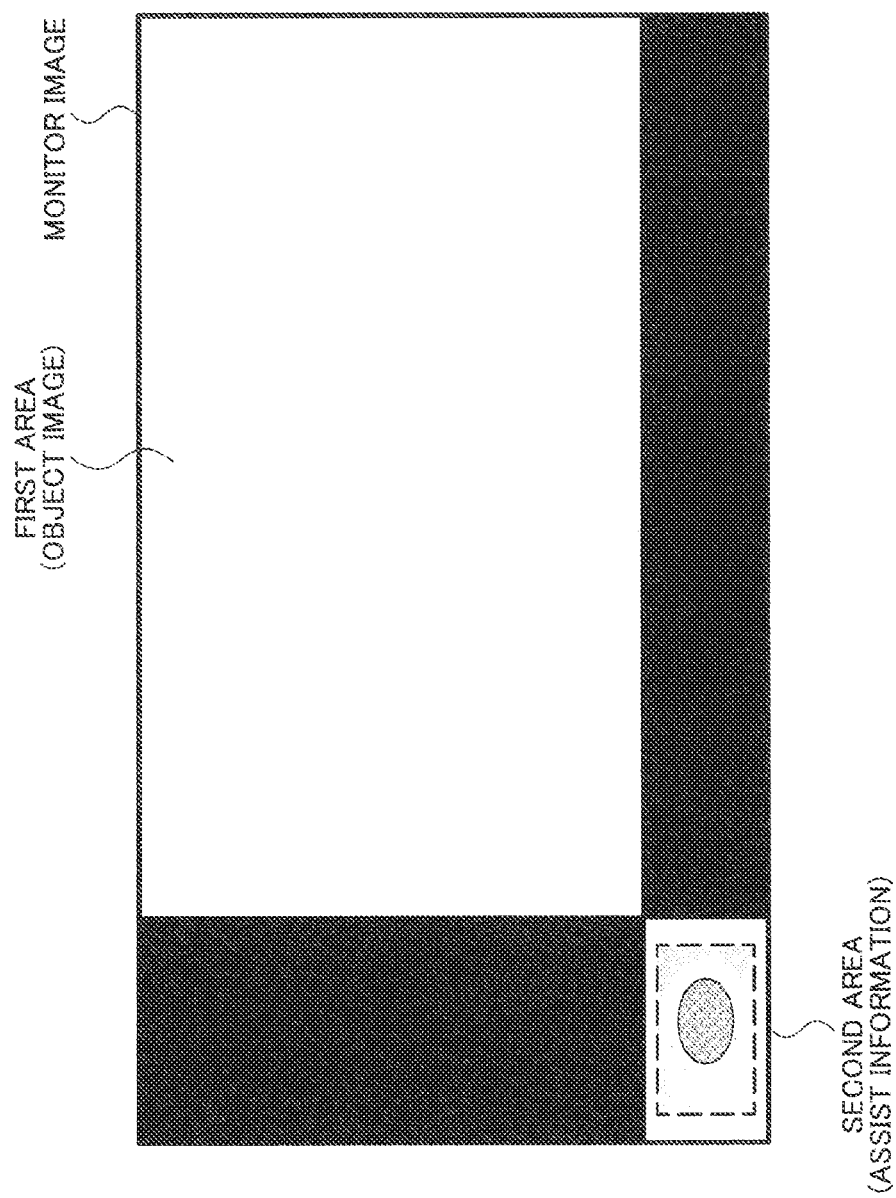

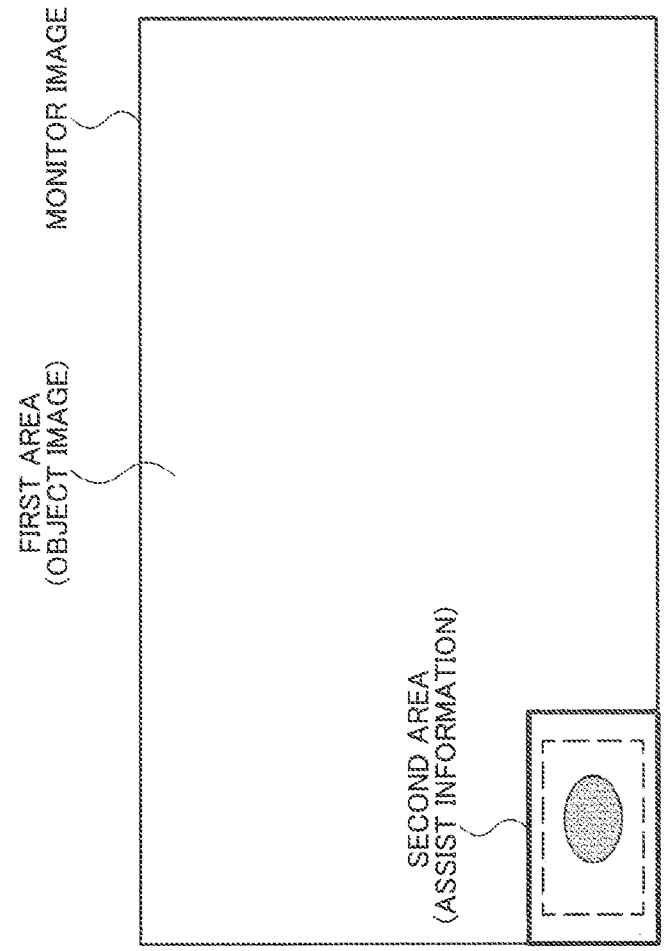

IMAGING DEVICE, ENDOSCOPE APPARATUS, AND METHOD FOR OPERATING IMAGING DEVICE

CROSS REFERENCE TO RELATED APPLICATION

This application is a continuation of International Patent Application No. PCT/JP2015/080245, having an international filing date of Oct. 27, 2015, which designated the United States, the entirety of which is incorporated herein by reference.

BACKGROUND

Manual focus adjustment is performed for surgical endoscopes used in a laparoscopic surgery. A user performs the focus adjustment by using a focus adjustment button and the like provided to the surgical endoscope, when a main subject is out of focus. The focus adjustment might be performed in a wrong direction due to a failure to determine whether the object is in a front focus state (on a near point side to be out of focus) or is in a back focus state (on a far point side to be out of focus) on a screen.

JP-A-2007-279334 discloses an example of a technique of an imaging device having a focus assist function. Specifically, whether a focus evaluation area in an image is in the front focus state or the back focus state is determined. Then, a direction in which a focus ring is rotated is displayed based on a result of the determination, to assist focus adjustment in the correct direction instinctively performed by the user.

In JP-A-2007-279334, assist information for bringing a predetermined subject area (focus evaluation area) into focus is displayed.

SUMMARY

According to one aspect of the invention, there is provided an imaging device comprising a processor, wherein the processor is configured to set a focus evaluation area in an object image obtained by an imaging section including an optical system in which an in-focus object plane position is changeable, control the in-focus object plane position based on operation input information in a manual focus mode, and control the in-focus object plane position based on a focus evaluation value obtained from an image of the focus evaluation area in an auto focus mode, output the object image to a display section, and detect an object shape based on the object image, wherein the processor is configured to implement, in the manual focus mode, setting the focus evaluation area to have a larger size than the focus evaluation area set in the auto focus mode, generating assist information assisting adjustment of the in-focus object plane position based on the focus evaluation value obtained from an image of the focus evaluation area set to have the larger size, and outputting the assist information on an area, in the object image, for which at least one of a position, a size, and a shape is controlled based on the object shape, to the display section.

According to another aspect of the invention, there is provided an endoscope apparatus comprising the imaging device.

According to another aspect of the invention, there is provided a method for operating an imaging device, the method comprising:

in a manual focus mode in which an in-focus object plane position of an imaging section is controlled based on operation input information, setting a focus evaluation area to have a larger size than the focus evaluation area set in an auto focus mode in which the in-focus object plane position is controlled based on a focus evaluation value of an object image obtained by the imaging section;

generating assist information assisting adjustment of the in-focus object plane position based on a focus evaluation value obtained from an image of the focus evaluation area, in the manual focus mode;

detecting an object shape based on the object image; and outputting the assist information on an area, in the object image, for which at least one of a position, a size, and a shape is controlled based on the object shape, and the object image to the display section, in the manual focus mode.

BRIEF DESCRIPTION OF THE DRAWINGS

FIG. 15 illustrates a third modification of the assist information and the method for displaying the assist information.

FIG. 16 illustrates a fourth modification of the assist information and the method for displaying the assist information.

DESCRIPTION OF EXEMPLARY EMBODIMENTS

Figure 1:
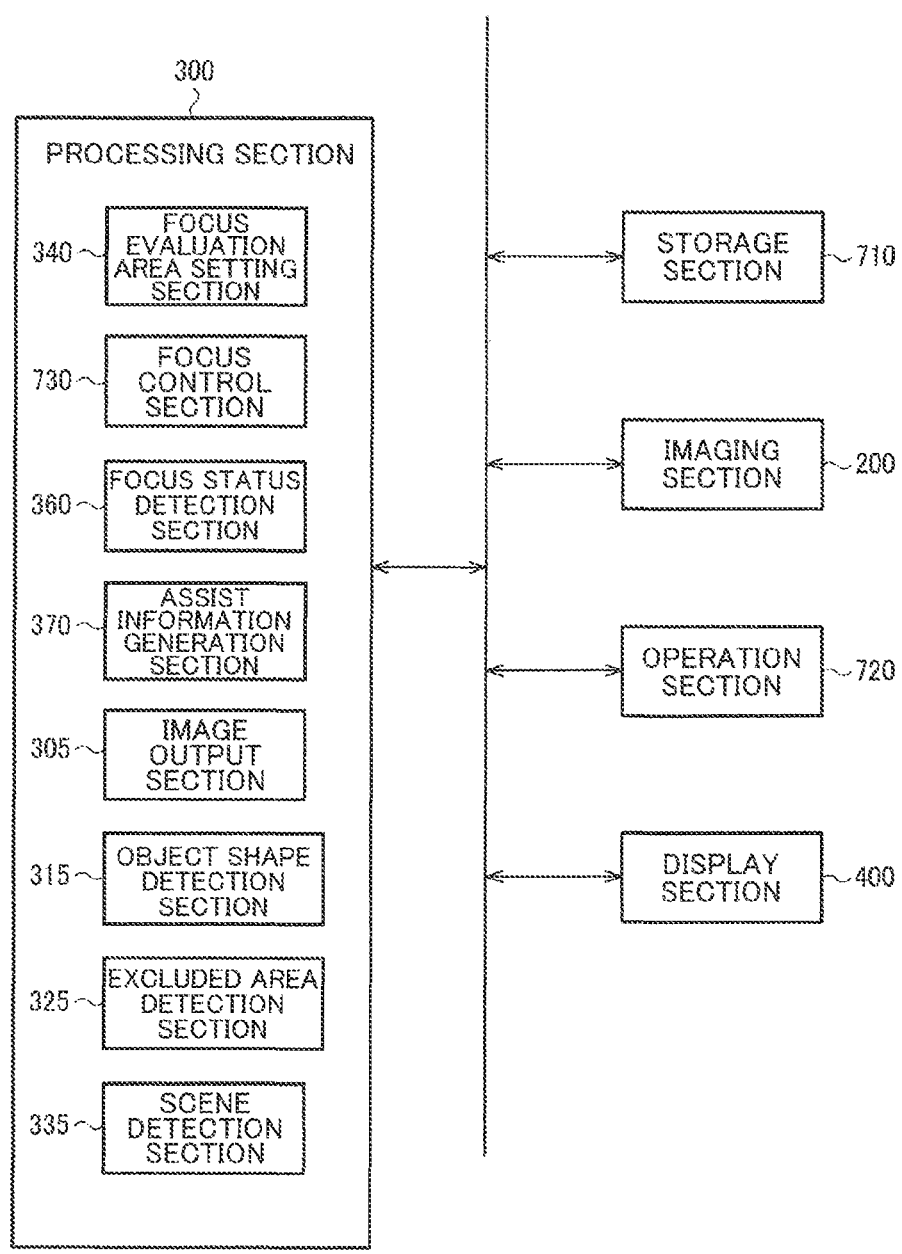
FIG. 1 illustrates a configuration example of an imaging device.

Some aspects of the present embodiment can provide an imaging device, an endoscope apparatus, a method for operating the imaging device, and the like with which assist information can be displayed for focus adjustment for an intended subject of manual focusing by a user.

According to one embodiment of the invention, there is provided an imaging device comprising a processor, wherein the processor is configured to set a focus evaluation area in an object image obtained by an imaging section including an optical system in which an in-focus object plane position is changeable, control the in-focus object plane position based on operation input information in a manual focus mode, and control the in-focus object plane position based on a focus evaluation value obtained from an image of the focus evaluation area in an auto focus mode, output the object image to a display section, and detect an object shape based on the object image, wherein the processor is configured to implement, in the manual focus mode, setting the focus evaluation area to have a larger size than the focus evaluation area set in the auto focus mode, generating assist information assisting adjustment of the in-focus object plane position based on the focus evaluation value obtained from an image of the focus evaluation area set to have the larger size, and outputting the assist information on an area, in the object image, for which at least one of a position, a size, and a shape is controlled based on the object shape, to the display section.

According to one aspect of the present embodiment, focus control can be performed in an auto focus mode and in a manual focus mode. In the manual focus mode, a focus evaluation area is set to have a larger size than the focus evaluation area set in the auto focus mode, and focus assist information for the focus evaluation area is displayed on a display section. With this configuration, assist information can be displayed for focus adjustment for an intended subject in manual focusing by a user.

The present embodiment will be described below. Note that the following exemplary embodiments do not in any way limit the scope of the invention laid out in the claims. Note also that not all of the elements described below in connection with the exemplary embodiments should be taken as essential elements of the invention.

An imaging device is described below as an example of a surgical endoscope apparatus. However, the present invention is not limited to this, and can be applied to various imaging devices (such as endoscope apparatuses for digestive organs and for industrial use, a microscope, a digital video camera, and a digital still camera, for example).

1. Imaging Device

Usually, when a user brings an object into focus in a manual focus mode, an imaging device is unaware of the position of the object desired to be brought into focus by the user. Thus, appropriate assist information for focus adjustment is difficult to display.

For example, in JP-A-2007-279334 described above, assist information (a rotation direction of a focus ring) for bringing a certain subject area (focus evaluation area) into focus is displayed. This subject area for which the assist information is provided might not match the object desired to be brought into focus by the user.

An endoscopic surgery is performed with a camera and a treatment tool inserted into a body through a plurality of holes. Treatment is performed by using the treatment tool while watching an image inside the body captured by the camera. The holes are small, and thus the camera inserted through such a hole has a limited operation range. With the operation range of the camera thus limited, the object of the user might be unable to be positioned at the center of the field of view. Thus, the object to be brought into focus might be in a peripheral section of the field of view. Such a situation is likely to lead to the mismatch between the object area for which the assist information is provided and the object desired to be brought into focus by the user.

In an endoscopic surgery, a user who is directly in charge of the surgery is different from a user who is in charge of operations on the camera including the focus adjustment. An instruction on the focus adjustment is verbally issued. Thus, there is a risk of discrepancy between the instruction and the actual operation, resulting in the surgery taking a long period of time. In view of this, the focus adjustment may be basically performed automatically (AF), and may be performed manually (MF) only when the AF results in a failure.

FIG. 1 illustrates a configuration example of an imaging device that can address the situation described above. The imaging device includes a processing section 300, a storage section 710, an imaging section 200, an operation section 720, and a display section 400. The processing section 300 includes a focus evaluation area setting section 340, a focus control section 730, an assist information generation section 370, an image output section 305, a focus status detection section 360, an object shape detection section 315, an excluded area detection section 325, and a scene detection section 335.

The processing section 300 (processor) controls various sections of the imaging device, and performs various types of information processing such as image processing. The processing section 300 is a processor including hardware as described later, for example.

For example, the storage section 710 (memory) stores image data corresponding to an image captured by the imaging section 200, setting data on the imaging device, and the like. The storage section 710 may also be used as a temporally storage memory (working memory) for the processing section 300.

For example, the imaging section 200 captures an image (movie, still image) and may include an image sensor, an optical system, a driving device that drives a focus mechanism of the optical system, and the like.

The operation section 720 is an input device enabling the user to operate the imaging device, and may include a button, a lever, a rotation ring, a mouse, a keyboard, a touch panel, and the like.

The display section 400 (display, display monitor) is a display device that displays an image captured by the imaging section 200 and an image as a result of processing performed by the processing section 300. Examples of the display section 400 include a liquid crystal display device, an electro-luminescence (EL) display device, and the like.

An operation of the imaging device according to the present embodiment is described below.

The imaging device according to the present embodiment includes the focus evaluation area setting section 340, the focus control section 730, the image output section 305, and the assist information generation section 370. The focus evaluation area setting section 340 sets a focus evaluation area in an object image obtained by the imaging section including an optical system in which an in-focus object plane position is changeable (focus adjustment can be performed). The focus control section 730 controls the in-focus object plane position (focus) based on operation input information in a manual focus mode, and controls the in-focus object plane position based on a focus evaluation value obtained from an image of the focus evaluation area in an auto focus mode. The image output section 305 outputs the object image to the display section 400.

In the manual focus mode, The focus evaluation area setting section 340 sets a focus evaluation area to have a larger size than the focus evaluation area set in the auto focus mode. The assist information generation section 370 generates assist information assisting adjustment of the in-focus object plane position based on the focus evaluation value obtained from an image of the focus evaluation area set to have the larger size. The image output section 305 outputs the assist information to the display section 400 (see FIG. 3, FIG. 10, and FIG. 11).

In the present embodiment, the focus evaluation area is set to have a larger size in the manual focus mode than the focus evaluation area set in the auto focus mode, and the assist information based on the focus evaluation area with the larger size is displayed. For example, in the auto focus mode, the focus evaluation area is set to be in a predetermined area that is relatively small such as a center portion of the image. In the present embodiment, the focus evaluation area in the manual focus mode is set to be larger than such a focus evaluation area. Thus, the assist information can be presented on a large area in the object image, and the user sees the assist information on a position to be in focus in the area, and can bring the position into focus. Thus, the position to be brought into focus is decided by the user, and the imaging device presents the assist information for a range of positions that may be selected by the user. Thus, the risk of mismatch between the object area provided with the assist information and the object desired to be brought into focus by the user is reduced.

The auto focus mode is usable to be maintained as long as auto focus adjustment is successfully performed for an object area desired to be monitored by the user, and to be switched to the manual focus mode by the user when the object area of the user is out of focus. Thus, the auto focus mode can be used to simplify the camera operation and shorten the time required for the surgery. Furthermore, the manual focus mode can also be used for enabling manual adjustment. For example, a manual focusing operation is performed for a case where stable focusing is preferred such as a case where a diseased part is monitored in detail or treated. In such a case, the assist information displayed in a large area enables the user to achieve quick focus adjustment for a desired subject.

The present embodiment may employ the following configuration. Specifically, the imaging section includes a memory (storage section 710) that stores therein information (a program and various types of data for example) and a processor (processing section 300, a processor including hardware) that operates based on the information stored in the memory. The processor sets the focus evaluation area in the object image. The processor controls an in-focus object plane position based on operation input information in the manual focus mode. The processor controls the in-focus object plane position based on a focus evaluation value in the auto focus mode. The processor outputs the object image to the display section 400. The processor sets the focus evaluation area to have a larger size in the manual focus mode than the focus evaluation area set in the auto focus mode. The processor generates assist information based on a focus evaluation value obtained from an image of the focus evaluation area, and outputs the assist information to the display section 400.

For example, the functions of the section of the processor (processing section 300) may each be implemented by individual hardware or may be implemented by integrated hardware. For example, the processor may include hardware, and the hardware may include at least one of a circuit that processes a digital signal and a circuit that processes an analog signal. For example, the processor may include one or a plurality of circuit devices (such as an integrated circuit (IC) for example) mounted on a circuit board, or one or a plurality of circuit elements (such as a resistor and a capacitor for example). The processor may be a central processing unit (CPU), for example. Note that the processor is not limited to the CPU. Various other processors such as a graphics processing unit (GPU) or a digital signal processor (DSP) may also be used. The processor may be a hardware circuit that includes an application specific integrated circuit (ASIC). The processor may include an amplifier circuit or a filter circuit that processes an analog signal. The memory (storage section 710) may be a semiconductor memory (e.g., SRAM or DRAM), or may be a register. The memory may be a magnetic storage device such as a hard disk drive (HDD), or may be an optical storage device such as an optical disc device, for example. For example, the memory stores a computer-readable instruction, and the function of each section of the processing section 300 is implemented by causing the processor to perform the instruction. The instruction may be an instruction set that is included in a program, or may be an instruction that instructs the hardware circuit included in the processor to operate. The sections of the processing section 300 include the image output section 305, an A/D conversion section 310, the object shape detection section 315, a pre-processing section 320, the excluded area detection section 325, an image processing section 330, the scene detection section 335, the focus evaluation area setting section 340, a focus evaluation value calculation section 350, the focus status detection section 360, the assist information generation section 370, an AF control section 380, a control section 390, and the focus control section 730.

For example, an operation according to the present embodiment is implemented as follows. Specifically, the imaging section 200 captures an image. The processing section 300 (processor) processes image data on the image, and resultant data is stored in the storage section 710 (memory). The focus evaluation area setting section 340 sets the focus evaluation area by referring to the size of the image (such as the number of pixels in vertical and horizontal directions), and stores information designating the area (such as coordinates of the four corners when the area is a rectangle, or the center coordinates and a radius when the area is a circle) in the storage section 710. The position and the size of the focus evaluation area may be set to be a predetermined position and size, or may be variably set in accordance with the situation or a user operation. The focus control section 730 reads the information on the focus evaluation area and the image data from the storage section 710, calculates a focus evaluation value in the focus evaluation area, and stores the value in the storage section 710. The focus evaluation value is an evaluation value for evaluating a focus status or a focusing level, and is a contrast value, an edge quantity, or the like.

The focus control section 730 stores a flag indicating each of the auto focus mode and the manual focus mode in the storage section 710. The sections of the processing section 300 refer the flag, and perform operations in each mode. In the auto focus mode, the focus control section 730 reads the focus evaluation value from the storage section 710, determines a control amount (including a movement direction and a movement amount) of a focus lens based on the focus evaluation value, and controls a focus lens driving section of the imaging section 200. The focus control section 730 switches the auto focus mode to the manual focus mode when the focus adjustment operation is performed through the operation section 720. In the manual focus mode, the focus control section 730 determines the control amount of the focus lens based on operation input information from the operation section 720, and controls the focus lens driving section of the imaging section 200.

In the manual focus mode, the focus status detection section 360 reads the focus evaluation value from the storage section 710, detects the focus status in the focus evaluation area based on the focus evaluation value, and stores information on the focus status in the storage section 710. Examples of the focus status, which is a status related to whether the object is in focus or out of focus, include a state where the object is in focus, a state where the object is out of focus, front focus/back focus in the out-of-focus state, and a focusing level. In the manual focus mode, the assist information generation section 370 reads the information on the focus status from the storage section 710, generates assist information based on the information on the focus status, and stores the assist information in the storage section 710. The assist information is information notifying the user of the direction (near point direction, far point direction) and an amount for the focus adjustment for bringing the object into focus. In the manual focus mode, the image output section 305 reads the assist information and the image data from the storage section 710, generates a display image from the information and the data, and outputs the display image to the display section 400. In the auto focus mode, the image output section 305 reads the image data from the storage section 710, generates a display image from the image data, and outputs the display image to the display section 400.

Figure 3:
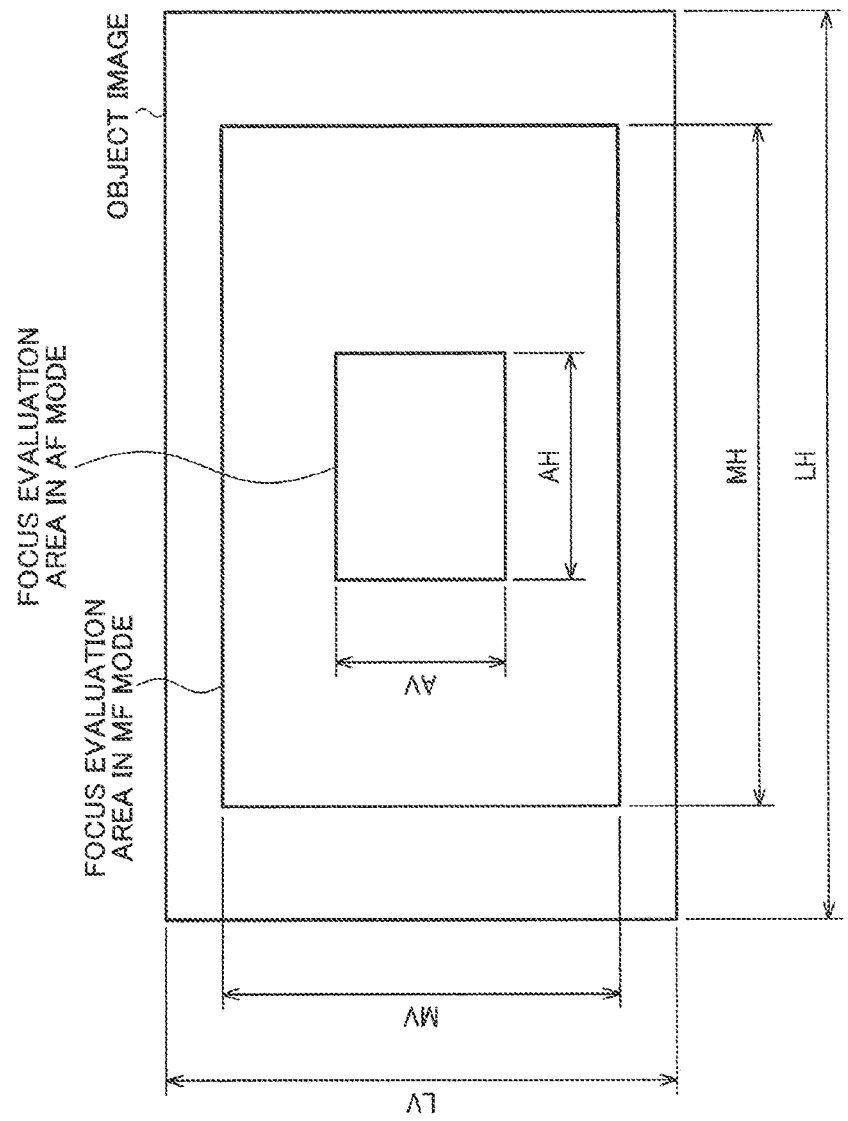
FIG. 3 illustrates a first setting example of a focus evaluation area.
Figure 4:
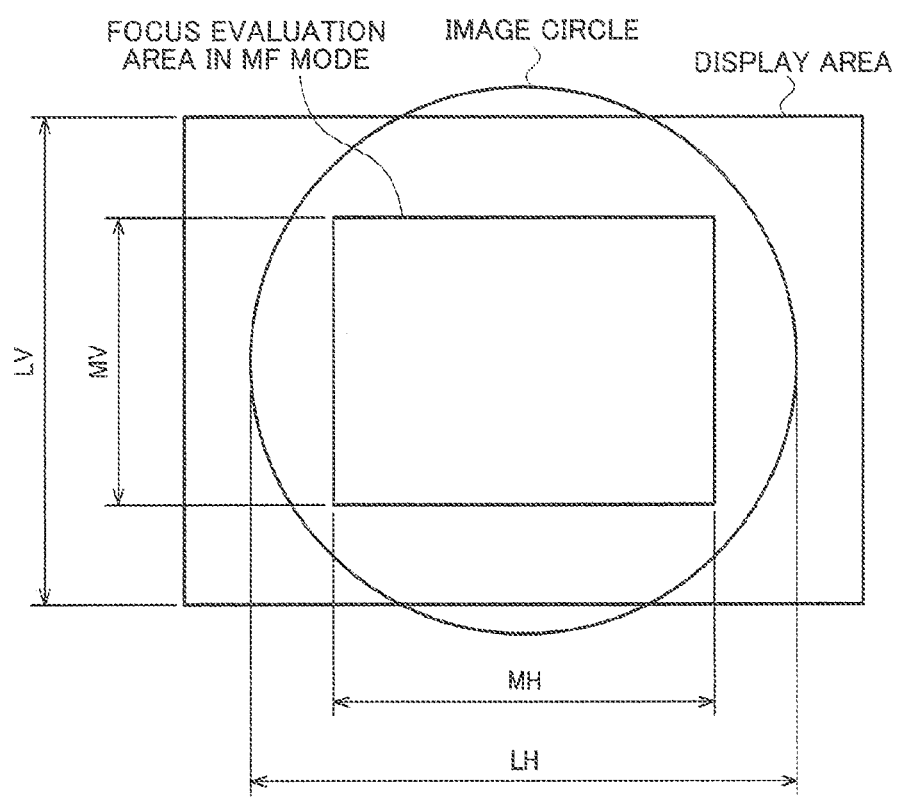
FIG. 4 illustrates a second setting example of a focus evaluation area.

In the present embodiment, in the manual focus mode, the focus evaluation area setting section 340 sets a focus evaluation area satisfying at least one of MH≥LH×50% and MV≥LV×50%, where LH represents a size of the object image in a horizontal scanning direction, LV represents a size of the object image in a vertical scanning direction, MH represents a size of the focus evaluation area in the horizontal scanning direction, and MV represents a size of the focus evaluation area in the vertical scanning direction (see FIG. 3 and FIG. 4).

In the present embodiment, the focus evaluation area with a size that is equal to or larger than 50% of the size of the object image is set. Thus, the focus status can be determined in a large range in the object image, instead of determining the focus status in a small range in the object image, and assist information on a large range in the object image can be presented to the user.

For example, the focus evaluation area is a rectangular area, and the lengths of the sides of the rectangle correspond to MH and MV. However, the focus evaluation area is not limited to the rectangular area, and may have any appropriate shape including an outlined area such as an area between a first rectangle and a second rectangle outside the first rectangle. If the focus evaluation area has such an appropriate shape, the maximum widths of the area in the horizontal and the vertical scanning directions respectively correspond to MH and MV. Alternatively, the focus evaluation area may include a plurality of separate areas. When this configuration is employed, the lengths of the sides of the smallest rectangle including the plurality of areas may correspond to MH and MV.

When the image is entirely occupied by the object (when the image circle is larger than the sensor size of the image sensor), the size of the object image corresponds to the size of the entire image. When the object occupies only a part of the image (when the image circle is smaller than the sensor size of the image sensor), the size of the object image corresponds to the size of the part occupied by the object. Note that the size of the object image may correspond to the size of the entire image, regardless of whether or not the image is entirely occupied by the object.

In the present embodiment, the imaging device includes the focus status detection section 360 that detects a focus status of each of areas in the image of the focus evaluation area based on the focus evaluation value. The assist information generation section 370 generates information indicating the focus status in each of the areas in the image of the focus evaluation area as the assist information, based on a result of determining the focus status (see FIG. 10 and FIG. 11).

Specifically, the focus status detection section 360 splits the focus evaluation area into a plurality of partial areas, and detects the focus status in each of the partial areas. The partial areas may each be an area including a plurality of pixels or may be an area including a single pixel. The assist information generation section 370 generates the assist information in each of the partial areas, and the image output section 305 displays the assist information on each of the partial areas.

In the present embodiment, the assist information on each area (each position) in the focus evaluation area is displayed. Thus, the user can obtain the assist information on any appropriate position in the focus evaluation area, and can quickly bring any subject of the user in the focus evaluation area into focus.

In the present embodiment, the focus status detection section 360 determines whether or not each of the areas in the focus evaluation area is on a near point side to be out of focus (front focus) or is on a far point side to be out of focus (back focus). The assist information generation section 370 generates, for an area determined to be on the near point side to be out of focus, information indicating that the area is on the near point side to be out of focus as the assist information, and generates, for an area determined to be on the far point side to be out of focus, information indicating that the area is on the far point side to be out of focus as the assist information (see FIG. 10 and FIG. 11).

In the present embodiment, the assist information indicating the front focus or the back focus is displayed for each position in the object image. Thus, the user can recognize an appropriate direction (toward the near point side or the far point side) of moving the focus for any appropriate position desired to be brought into focus. Thus, the user can quickly bring the desired subject into focus.

The state of being on the near point side to be out of focus is a state where an object is closer to the camera than an in-focus subject to be out of focus. The state of being on the far point side to be out of focus is a state where an object is farther from the camera than an in-focus subject to be out of focus.

The focus status detection section 360 may further determine whether or not each area in the focus evaluation area is in focus. For an area determined to be in focus, the assist information generation section 370 may generate assist information indicating that the area is in focus.

In the present embodiment, in the manual focus mode, the focus evaluation area setting section 340 sets the focus evaluation area to have the center positioned at the center of the object image (see FIG. 3 and FIG. 4).

In an endoscopic surgery, the object to be monitored is set to be at a position close to the center of the field of view as much as possible in many cases (for example, a treatment target part is set to be close to the center of the field of view).

In view of this, the focus evaluation area is set to have the center matching the center of the object image, so that the assist information can be provided for an area that is likely to be desired to be brought into focus by the user.

For example, the center of the object image is an intersecting point between diagonal lines of a rectangular image, the center of the image circle, or the like. The center of the focus evaluation area is an intersecting point between diagonal lines of a rectangular area, the center of a circular area, or the like. Note that the intersecting point and the center do not necessarily match.

In the present embodiment, in the manual focus mode, the image output section 305 outputs the assist information on an area, in the object image, for which at least one of the position, the size, and the shape is controlled based on the object image (see FIG. 6 to FIG. 9C, FIG. 13, and FIG. 14).

For example, for an object with a large depth such as a lumen, the assist information may be displayed for an object relatively close to the camera such as a wall surface or the like on a near side (near point side) of the lumen. For an object having a protruding shape such as an organ in outer view, the assist information may be displayed for the protruding portion (that is, the organ).

In the present embodiment, at least one of the position, the size, and the shape of the area for which the assist information is displayed is controlled in accordance with the object in the captured image. Thus, the assist information can be provided to an area that is likely to be desired to be brought into focus by the user in accordance with the object.

The area for which the assist information is output may be controlled in any stage in a series of processes from generating the assist information from the object image to displaying the information. The control may be performed as follows for example.

For example, in the manual focus mode, the focus evaluation area setting section 340 controls at least one of the position, the size, and the shape of the focus evaluation area based on the object image. The assist information generation section 370 generates the assist information on the focus evaluation area. The image output section 305 outputs the assist information on the focus evaluation area (see FIG. 6 to FIG. 9C).

As a result of the focus evaluation area setting section 340 thus controlling the focus evaluation area, the area displaying the assist information may be controlled.

Alternatively, the assist information generation section 370 controls at least one of the position, the size, and the shape of an assist information generated area for which the assist information is generated, based on the object image. The image output section 305 outputs the assist information on the assist information generated area (see FIG. 13 and FIG. 14).

For example, the assist information generated area may be set in the focus evaluation area set to be a predetermined area.

As a result of the assist information generation section 370 thus controlling the assist information generated area regardless of whether or not the focus evaluation area is controlled, the area displaying the assist information may be controlled.

Figure 13:
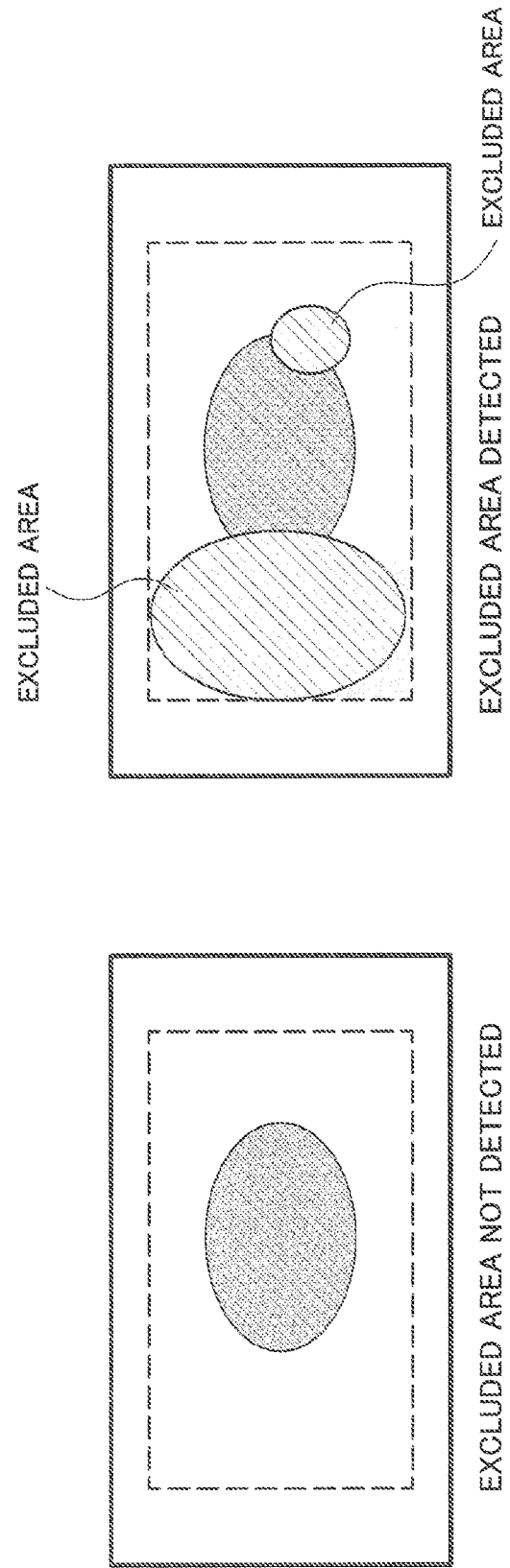
FIG. 13 is a diagram illustrating an operation of excluded area detection section and an operation of the assist information generation section based on a result of the excluded area detection.
Figure 14:
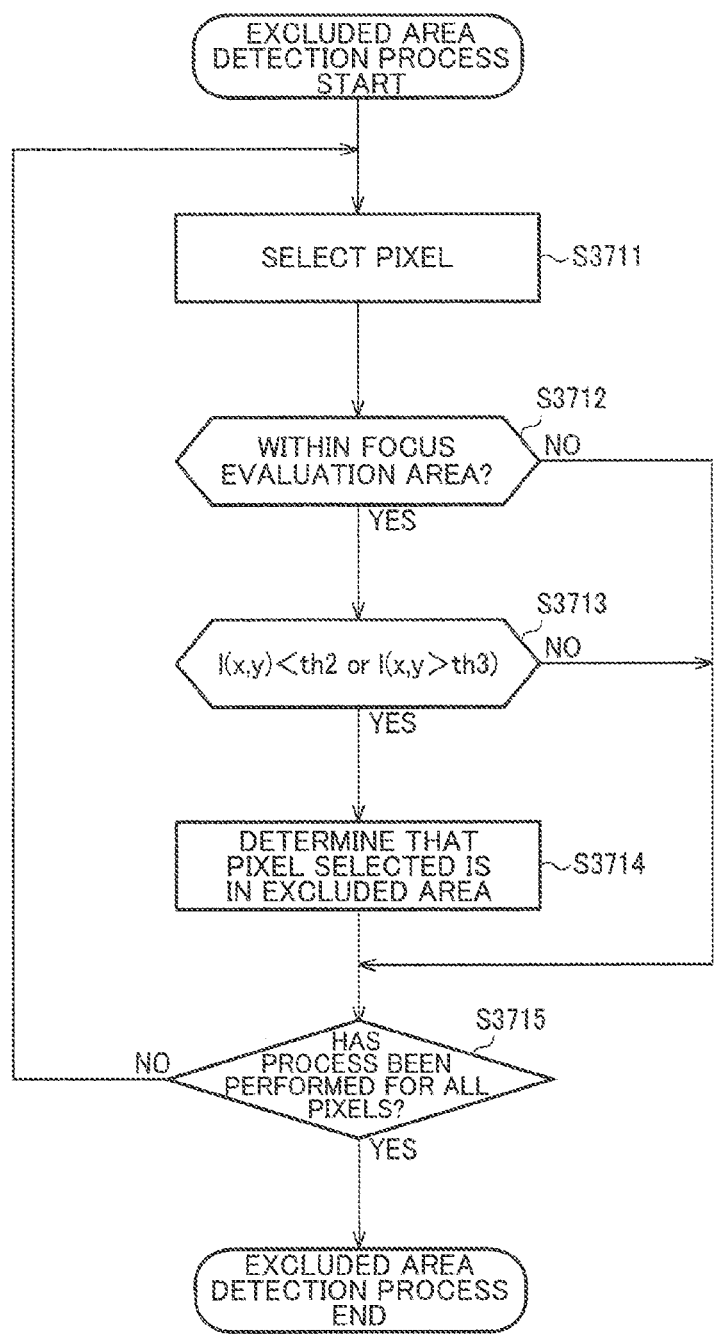
FIG. 14 is a flowchart illustrating an excluded area detection process.

Alternatively, the image output section 305 may control at least one of the position, the size, and the shape of an assist information display area for which the assist information is displayed, based on the object image, and may output the assist information on the assist information display area (see FIG. 13 and FIG. 14).

For example, the assist information display area may be set in the focus evaluation area or the assist information generated area set to be a predetermined area. For example, the assist information generated area may be the same as the focus evaluation area.

As a result of the image output section 305 thus controlling the assist information display area regardless of whether or not the focus evaluation area or the assist information generated area is controlled, the area on which the assist information is displayed may be controlled.

In the present embodiment, the imaging device includes an object shape detection section 315 that detects the object shape based on the object image. In the manual focus mode, the image output section 305 outputs the assist information on an area for which at least one of the position, the size, and the shape is controlled based on the object shape (see FIG. 6 to FIG. 9C).

Specifically, in the manual focus mode, the focus evaluation area setting section 340 controls at least one of the position, the size, and the shape of the focus evaluation area based on the object shape. The image output section 305 outputs the assist information on the focus evaluation area (see FIG. 6 to FIG. 9C). However, this should not be construed in a limiting sense, and the area may be controlled based on the object shape in any stage in a series of processes from generating the assist information from the object image to displaying the information.

For example, for an object with a large depth such as a lumen, the shape information on an area on a far side (far point side) or an area such as a wall surface on the near side (near point side) of the lumen may be detected. For an object having a protruding shape such as an organ in outer view, an area on the protruding portion (that is, the organ) or an area not on the protruding portion may be detected as the shape information. Various methods may be employed for shape detection. For example, the shape may be detected based on correlation between the distance from an emission lens of an illumination and the brightness of the object, the shape may be detected by pattern recognition process or the like, or the shape may be detected by three-dimensional measurement or the like.

In the present embodiment, at least one of the position, the size, and the shape of the area for which the assist information is displayed is controlled based on the object shape. Thus, the assist information can be provided to an area that is likely to be desired to be brought into focus by the user, in accordance with the object shape.

In the present embodiment, the imaging device includes the excluded area detection section 325 that detects an excluded area for which the assist information is not displayed, based on the object image. In the manual focus mode, the image output section 305 outputs the assist information on the area for which at least one of the position, the size, and the shape is controlled based on information on the excluded area (see FIG. 13 and FIG. 14).

Specifically, the assist information generation section 370 generates the assist information on the assist information generated area as a result of excluding the excluded area from the focus evaluation area (see FIG. 13 and FIG. 14). However, this should not be construed in a limiting sense, and the area control based on the excluded area may be performed in any stage in a series of processes from generating the assist information from the object image to displaying the information.

For example, the excluded area detection section 325 detects the excluded area based on the brightness, the contrast, the saturation, or the like of the image. For example, an area with excessively high or low brightness such as a highlight portion or a shadow portion, an area with excessively low contrast such as a flat portion (area where the contrast does not change as a result of wobbling or the like), an area with excessively low saturation such as a local portion with mist, or the like is detected as the excluded area.

In the present embodiment, at least one of the position, the size, and the shape of the area for which the assist information is displayed is controlled based on the excluded area. Thus, an excluded area that is less likely to be desired to be brought into focus (monitored) by the user can be excluded from the assist information display area. The assist information might hinder visual recognition of the object, and thus is preferably prevented from being displayed on an unnecessary portion as much as possible.

In the present embodiment, the imaging device includes the scene detection section 335 that detects a scene based on the object image. The assist information generation section 370 generates the assist information based on the scene (see FIG. 12). Specifically, the assist information generation section 370 may determine whether or not to generate the assist information based on the scene. When the assist information is generated, the image output section 305 may output the assist information.

Figure 12:
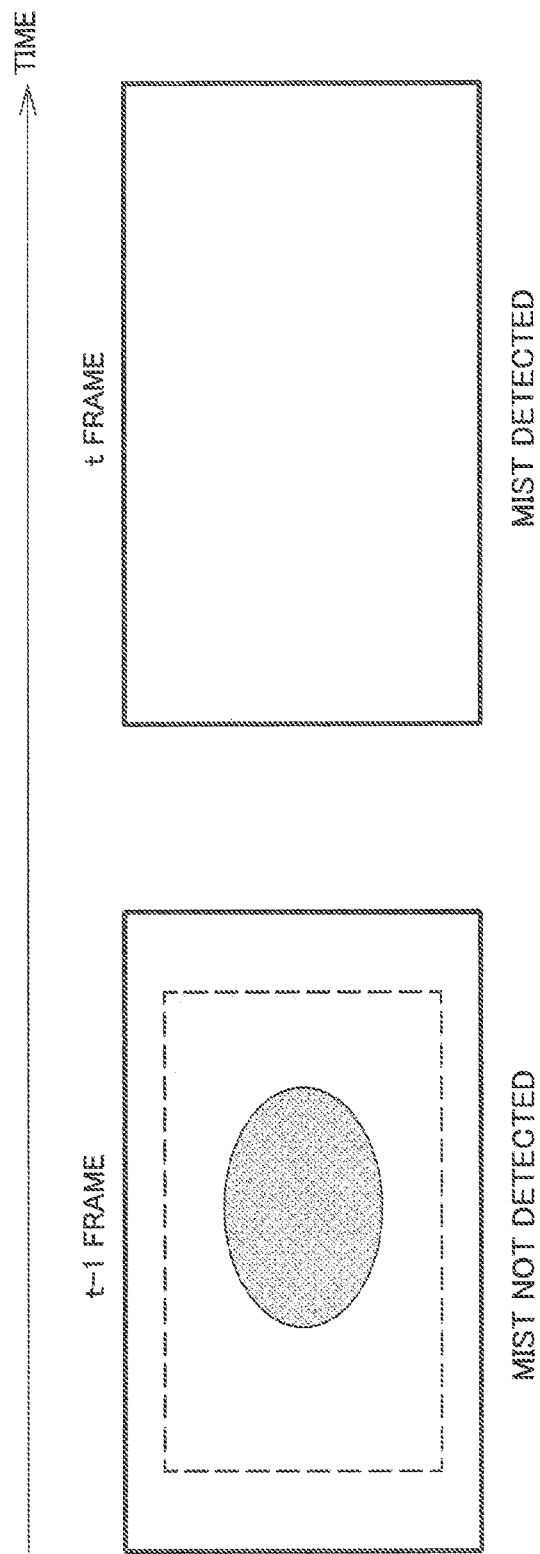
FIG. 12 is diagram illustrating an operation of a scene detection section and an operation of an assist information generation section based on a result of the scene detection.

Alternatively, the image output section 305 may output the assist information based on the scene (see FIG. 12). Specifically, the image output section 305 may determine whether or not to output the assist information, generated regardless of the scene, based on the scene.

For example, when a predetermined scene is detected, the assist information may or may not be generated or output. Alternatively, when a change in a scene is detected, the generation or output of the assist information may be started or stopped.

Various methods may be employed for scene detection. For example, a scene or a scene change may be detected by detecting a motion vector or the like, by detecting the brightness, color, saturation, contrast, or the like of an image, or by performing pattern recognition on an image.

In the present invention, whether or not to display the assist information can be determined based on a scene or a scene change Thus, for example, the assist information may be displayed for a scene requiring focus adjustment (such as a scene where an image capturing area is to be moved for example) and may not be displayed for a scene where the focus adjustment is disabled (such as a scene where the object is less visible due to mist or the like). Thus, the assist information may be adaptively presented as appropriate. The assist information might hinder visual recognition of the object, and thus is preferably prevented from being displayed as much as possible in a situation where no assist information required.

Figure 10:
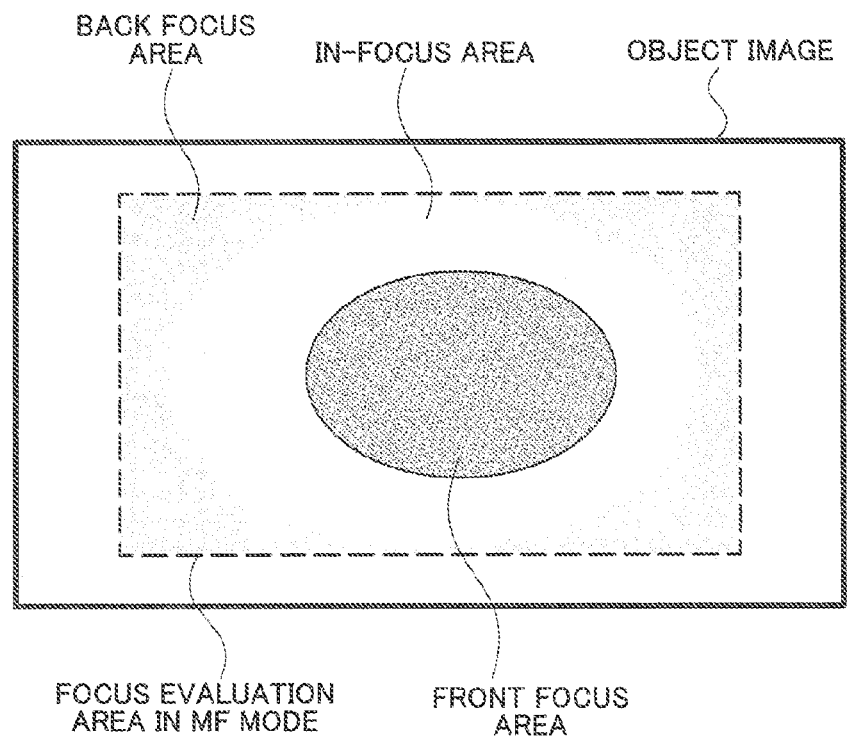
FIG. 10 illustrates an example of assist information and a method for displaying the assist information.
Figure 11:
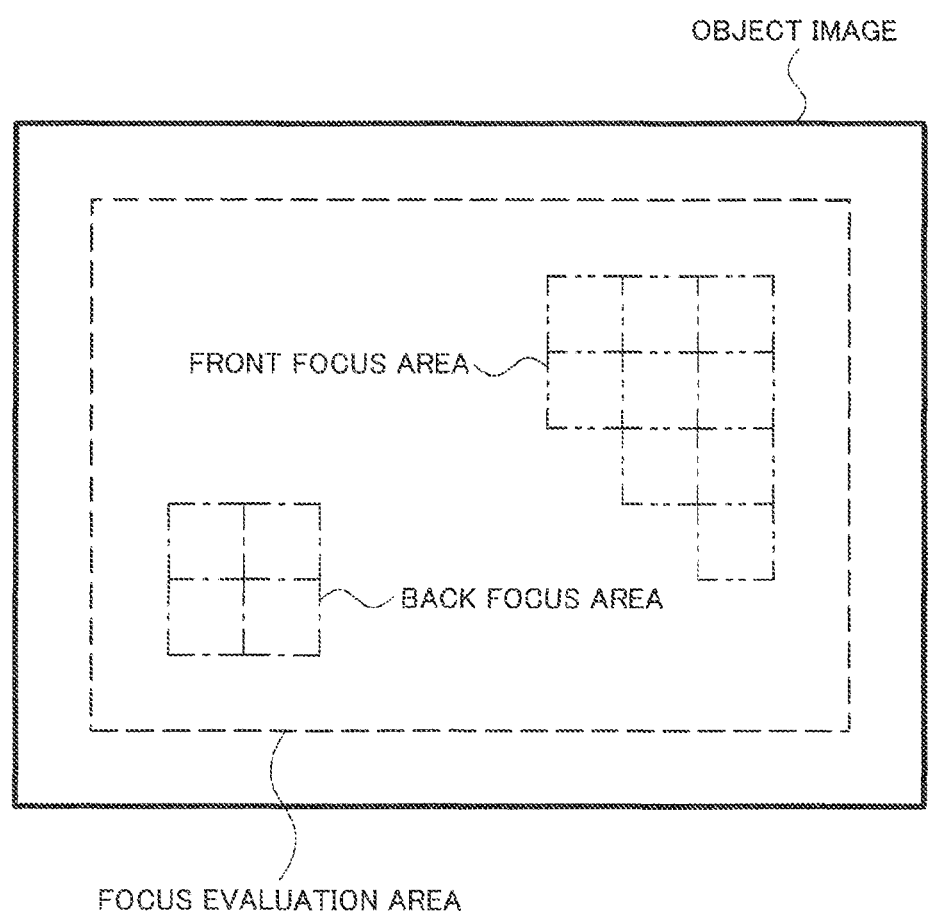
FIG. 11 illustrates a second modification of the assist information and the method for displaying the assist information.

In the present embodiment, the image output section 305 displays the assist information on each of areas in the object image to be overlapped with the areas in the object image (see FIG. 10 and FIG. 11).

For example, the object image is split into a plurality of partial areas, and assist information on each of the partial areas is generated. Then, the assist information on a certain partial area is displayed to be overlapped with an image of the partial area. Examples of the assist information to be overlapped with the object image includes a semitransparent color in the partial area, hatching in the partial area, a frame surrounding the partial area, a frame surrounding outer circumferences of a plurality of partial areas with the same focus status (front focus or back focus), a graphic of an arrow or the like corresponding to the focus status (front focus or back focus), and the like.

In the present embodiment, the assist information is displayed for each area (each position) in the object image. Thus, the user can obtain the assist information on any appropriate position in the object image (actually, in the focus evaluation area). Thus, any subject of the user desired to be brought into focus can be quickly brought into focus.

In the present embodiment, the image output section 305 displays the object image and the assist information respectively in a first area and a second area different from the first area, in a display area of the display section 400 (see FIG. 15).

Alternatively, the image output section 305 may display the object image and the assist information respectively in the first area and the second area inside the first area, in the display area of the display section 400 (see FIG. 16).

In the present embodiment, the object image and the assist information are separately displayed in first and the second areas, instead of displaying the assist information on the object image in an overlapping manner. Thus, the assist information can be provided to assist the focus adjustment, without compromising the visibility of the object image.

In the present embodiment, in the manual focus mode, the image output section 305 hides the assist information when the in-focus object plane position is not adjusted for a predetermined period of time (when the focus adjustment is not performed for a predetermined period of time), and displays the assist information when the in-focus object plane position is adjusted (when the focus adjustment is performed) after the assist information has been hidden.

For example, the assist information is hidden when no operation input to a button or a rotation ring for focus adjustment, provided to the operation section 720, is detected for a predetermined period of time.

Thus, the assist information can be hidden when the user determines that no focus adjustment is required and can be displayed when the user wants to perform the focus adjustment. For example, the assist information might hinder a treatment or detailed monitoring. In such a situation, the focus is basically maintained and thus the assist information may be hidden.

2. Endoscope Apparatus

Figure 2:
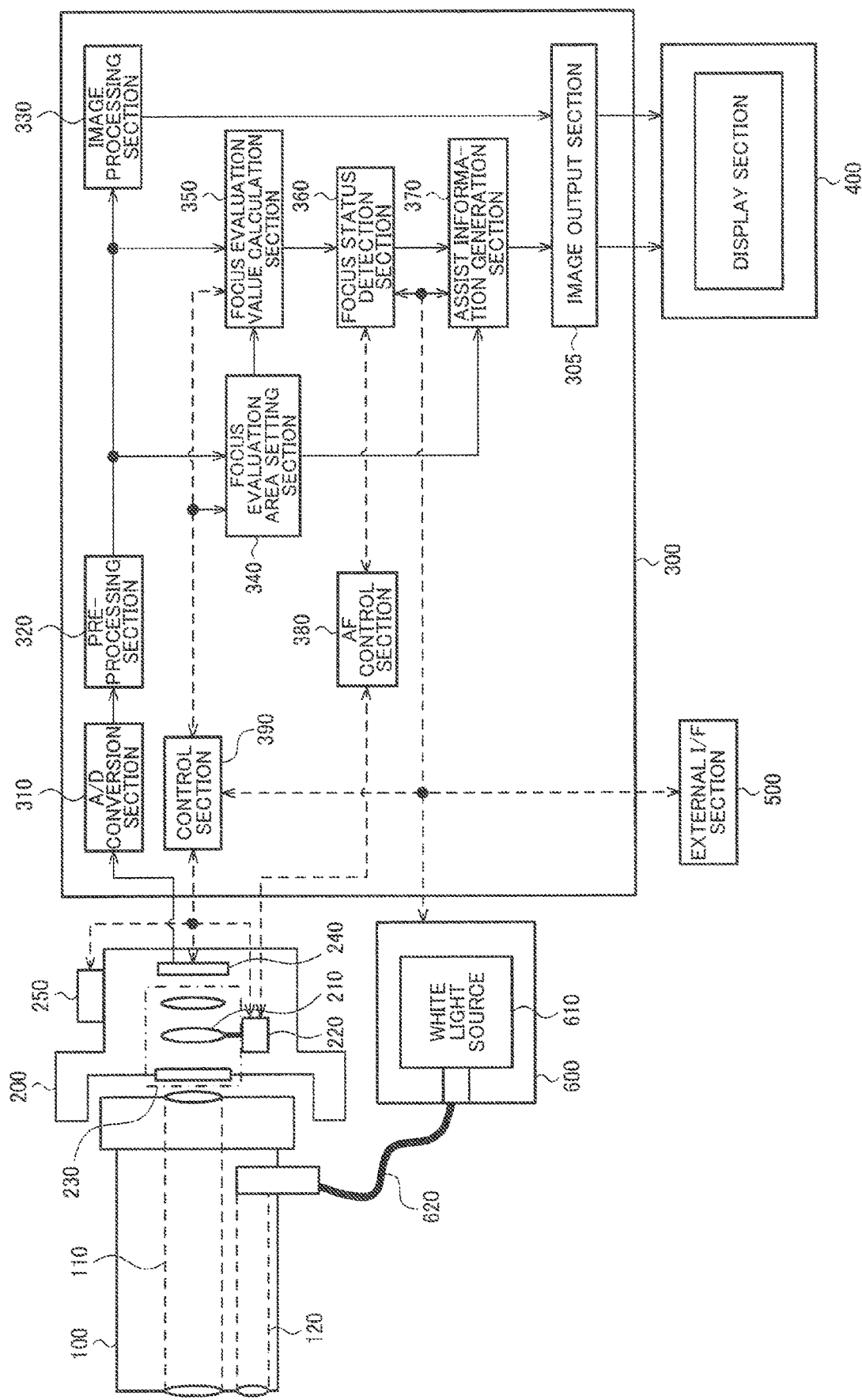
FIG. 2 illustrates a configuration example of an endoscope apparatus.

A configuration and an operation in a case where the imaging device described above is applied to an endoscope apparatus (surgical endoscope apparatus) are described in detail below. FIG. 2 illustrates a configuration example of the endoscope apparatus. The endoscope apparatus includes a rigid scope 100, the imaging section 200, the processing section 300, the display section 400, an external interface (I/F) section 500, and a light source section (light source device) 600.

For example, the rigid scope 100, the imaging section 200, the processing section 300, the display section 400, and the light source section 600 are respectively provided as a rigid scope, a camera head, a video processor (processing device), a display, and a light source device as individual devices. The rigid scope is detachably attached to the camera head with a chuck mechanism provided to the camera head. The camera head, the display, and the light source device are each connected to the video processor via a cable. The rigid scope is connected to the light source device via a light guide cable. Note that the configuration of the imaging device and the endoscope apparatus is not limited to this.

Configurations and operations of the sections are described below. A focus lens operation section 250 and the external I/F section 500 correspond to the operation section 720. The AF control section 380 and the control section 390 correspond to the focus control section 730. The storage section 710 is omitted in FIG. 2.

The rigid scope 100 is inserted into the body. The rigid scope 100 includes a lens system 110 and a light guide section 120.

The lens system 110 includes an imaging lens, a relay lens, an eyepiece, and the like.

The light guide section 120 guides light, emitted from a light guide cable 620, to a distal end of the rigid scope 100.

The imaging section 200 forms an image from reflected light from the object. The imaging section 200 includes a focus lens 210, a focus lens driving section 220, an objective lens system 230, an image sensor 240, and the focus lens operation section 250.

The focus lens 210 is a lens for adjusting an in-focus object plane position (focus).

The focus lens driving section 220 drives the focus lens 210 (moves the position of the focus lens 210). The focus lens driving section 220 is a voice coil motor (VCM), for example.

The objective lens system 230 forms an optical image from reflected light that is light emitted from the light guide section 120 and reflected on the object (forms an optical image of the object).

The image sensor 240 photoelectrically converts the reflected light for forming the optical image with the objective lens system 230 into an image.

The focus lens operation section 250 is an interface with which the user performs focus adjustment. The user operates the focus lens operation section 250 to drive the focus lens 210 to adjust the in-focus object plane position. For example, the focus lens operation section 250 includes a button for moving the focus toward the near point side and a button for moving the focus toward the far point side. Alternatively, the interface may be a focus ring, a mouse wheel, or a click wheel.

The processing section 300 performs signal processing including image processing. The processing section 300 includes the image output section 305, the A/D conversion section 310, the pre-processing section 320, the image processing section 330, the focus evaluation area setting section 340, the focus evaluation value calculation section 350, the focus status detection section 360, the assist information generation section 370, the AF control section 380, and the control section 390.

The A/D conversion section 310 converts analog signals sequentially output from the image sensor 240 into digital images and sequentially outputs the digital images to the pre-processing section 320.

The pre-processing section 320 performs image processing including white balance, an interpolation process (demosaicing process), and the like on the images output from the A/D conversion section 310, and sequentially outputs the resultant images to the image processing section 330, the focus evaluation area setting section 340, and the focus evaluation value calculation section 350.

The image processing section 330 performs image processing including color conversion, gray scale conversion, edge enhancement, a scaling process, a noise reduction, and the like on the images output from the pre-processing section 320, and sequentially outputs the resultant images to the display section 400.

The focus evaluation area setting section 340 sets the focus adjustment area for an image output from the pre-processing section 320, and outputs the focus evaluation area to the focus evaluation value calculation section 350 and the assist information generation section 370. The focus evaluation area setting section 340 determines whether the current mode is an auto focus mode (AF mode) or a manual focus mode (MF mode) based on a control signal from the control section 390, and sets a larger focus evaluation area in the MF mode than in the AF mode (see FIG. 3).

The focus evaluation value calculation section 350 calculates the focus evaluation value from the object image in the focus evaluation area, and outputs the value to the focus status detection section 360. For example, the focus evaluation value is a bandpass filter output.

The focus status detection section 360 detects the focus status (in-focus, front focus, back focus) based on the focus evaluation value output from the focus evaluation value calculation section 350 and on a focus lens driving signal from control section 390, and outputs to focus status to the assist information generation section 370. For example, the control section 390 causes a wobbling operation of the focus lens 210, and the focus evaluation value calculation section 350 detects the focus status based on the focus evaluation value obtained during the wobbling operation. The focus status detection method is not limited to this. The image sensor 240 may include phase difference pixels, and the focus status may be detected from an output value from the phase difference pixels. In such a configuration, the focus evaluation value corresponds to the output value from the phase difference pixels.

The assist information generation section 370 generates the assist information to be displayed on the display section 400, based on the focus evaluation area set by the focus evaluation area setting section 340 and the focus status output from the focus status detection section 360, only in the MF mode (see FIG. 10).

In the AF mode, the image output section 305 outputs the object image to the display section 400. In the MF mode, the image output section 305 outputs the object image and the assist information to the display section 400. The assist information may be displayed to be overlapped with the object image (FIG. 10), may be displayed in an area different from an area where the object image is displayed (FIG. 15), or may be displayed in a part of the object image (FIG. 16). More preferably, the assist information is displayed only while the focus lens operation section 250 is being operated, and is hidden if the focus lens operation section 250 is not operated for a predetermined period of time. With this configuration, the assist information can be displayed only while the in-focus object plane position adjustment, requiring the assist information, is in progress, whereby a load on the user can be reduced.

In the AF mode (determined based on the control signal from the control section 390), the AF control section 380 controls the focus lens driving section 220 based on the focus status output from the focus status detection section 360, to bring the object into focus. For example, known techniques such as wobbling or hill climbing may be employed for the AF control.

The control section 390 is connected to the external I/F section 500, the image processing section 330, the AF control section 380, and the image sensor 240 to exchange a control signal. The control section 390 switches between the MF mode and the AF mode, based on whether or not the user has operated the focus lens operation section 250. For example, when the focus lens operation section 250 is operated in the AF mode, the AF mode is switched to the MF mode. Then, when an AF mode setting button (provided to the focus lens operation section 250 or the external I/F section 500) is pressed or when a predetermined period of time has elapsed with no operation on the focus lens operation section 250, the MF mode is switched to the AF mode. In the MF mode, the control section 390 controls the focus lens driving section 220, based on an operation input via the focus lens operation section 250, to move the focus lens 210.

The display section 400 sequentially displays the object images, output from the image processing section 330, and the assist information, output from the assist information generation section 370. For example, the display section 400 is a liquid crystal monitor.

The external I/F section 500 is an interface used for input to the endoscope apparatus by the user or the like. For example, the external I/F section 500 includes a setting button for setting the position and the size of the focus evaluation area in the AF mode and an adjustment button for adjusting a parameter for image processing.

3. Focus Evaluation Area Setting Section

FIG. 3 illustrates a first setting example of the focus evaluation area. The focus evaluation area setting section 340 determines whether the current mode is the AF mode or the MF mode based on the control signal from the control section 390, and sets the focus evaluation area, corresponding to the current mode, on the object image.

The focus evaluation area in the AF mode is set to be at the center of the object image and to have a predetermined size in initial setting. The position and the size of the focus evaluation area are changed with the user operating the external I/F section 500. The lengths (sizes) of the focus evaluation area in the AF mode in the horizontal and the vertical scanning directions are respectively denoted with AH and AV.

The focus evaluation area in the MF mode is set to have a size that is 60% of the entire subject image, in each of the horizontal scanning direction and the vertical scanning direction. Specifically, the MH≥60%×LH and MV≥60%×LV are satisfied, where LH and LV represent the lengths of the sides of the object image respectively in the horizontal scanning direction and the vertical scanning direction, and MH and MV represent the lengths of the sides of the focus evaluation area respectively in the horizontal scanning direction and the vertical scanning direction. Furthermore, MH>AH and MV>AV are satisfied. However, the focus evaluation area is not limited to the 60% size, and can be set to have any size as long as the focus evaluation area has a size that is equal to or larger than 50% of the entire subject image in the horizontal scanning direction or the vertical scanning direction (MH≥50%×LH and MV≥50%×LV are satisfied), and is set to be larger than the size in the AF mode (MH>AH and MV>AV are satisfied). In the MF mode, the focus evaluation area is positioned at the center of the object image. With the focus evaluation area thus set in the MF mode, the object that has failed to be brought into focus in the AF mode can be provided within the focus evaluation area. Thus, assist information assisting the focus adjustment for the object can be generated.

FIG. 4 illustrates a second setting example of the focus evaluation area. Specifically, FIG. 4 illustrates a setting example in a case where the image circle is smaller than the image size (display area). As in the first setting example, MH>AH and MV>AV are satisfied.

For example, when the diameter of the image circle is smaller than the image size in the horizontal scanning direction, the length of the side of the focus evaluation area in the horizontal scanning direction is set to satisfy MH≥50%×LH, where LH represents the diameter of the image circle. Thus, a smaller one of the image size and the diameter of the image circle is set as the size of the object image. The same applies to the vertical scanning direction.

4. Subject Shape Detection Section

Figure 5:
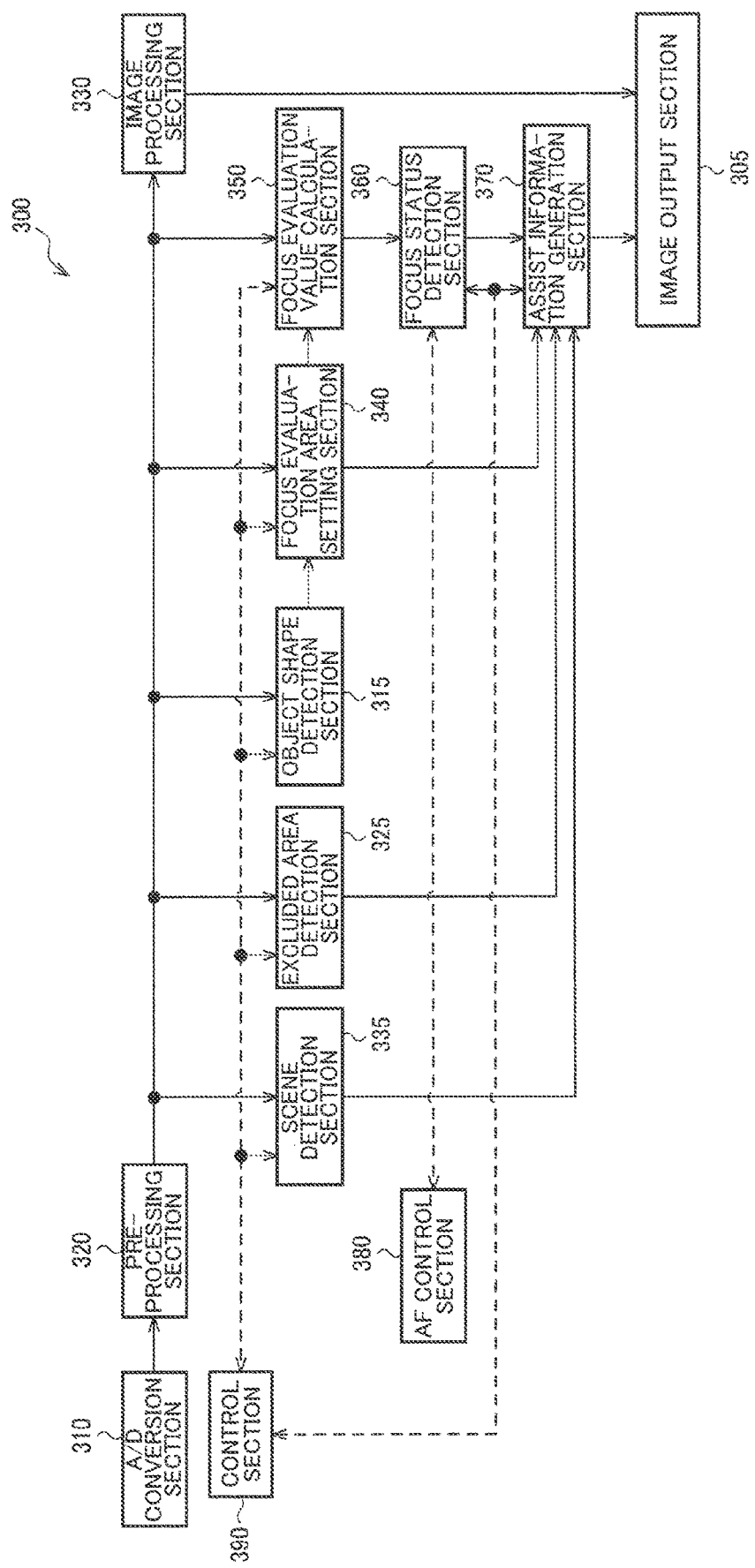
FIG. 5 illustrates a second configuration example of a processing section.

FIG. 5 illustrates a second configuration example of the processing section 300. The processing section 300 includes the object shape detection section 315, the excluded area detection section 325, the scene detection section 335, the image output section 305, the A/D conversion section 310, the pre-processing section 320, the image processing section 330, the focus evaluation area setting section 340, the focus evaluation value calculation section 350, the focus status detection section 360, the assist information generation section 370, the AF control section 380, and the control section 390. Note that only one of the object shape detection section 315, the excluded area detection section 325, and the scene detection section 335 or any two of the sections may be provided. Components that have been described above with reference to FIG. 2 are denoted with the same reference numerals, and the description thereof is omitted as appropriate.

An operation of the focus evaluation area setting section 340 based on an operation of the object shape detection section 315 and a result of the objection shape detection is described. In the description below, the focus evaluation area setting section 340 controls the focus evaluation area based on a result of the object shape detection. However, this should not be construed in a limiting sense, and the assist information generation section 370 may control the assist information generated area, which is an area for which the assist information is generated, based on a result of the object shape detection. Furthermore, the image output section 305 may control the assist information display area, which is an area on which the assist information is displayed, based on a result of the object shape detection.

Figure 6:
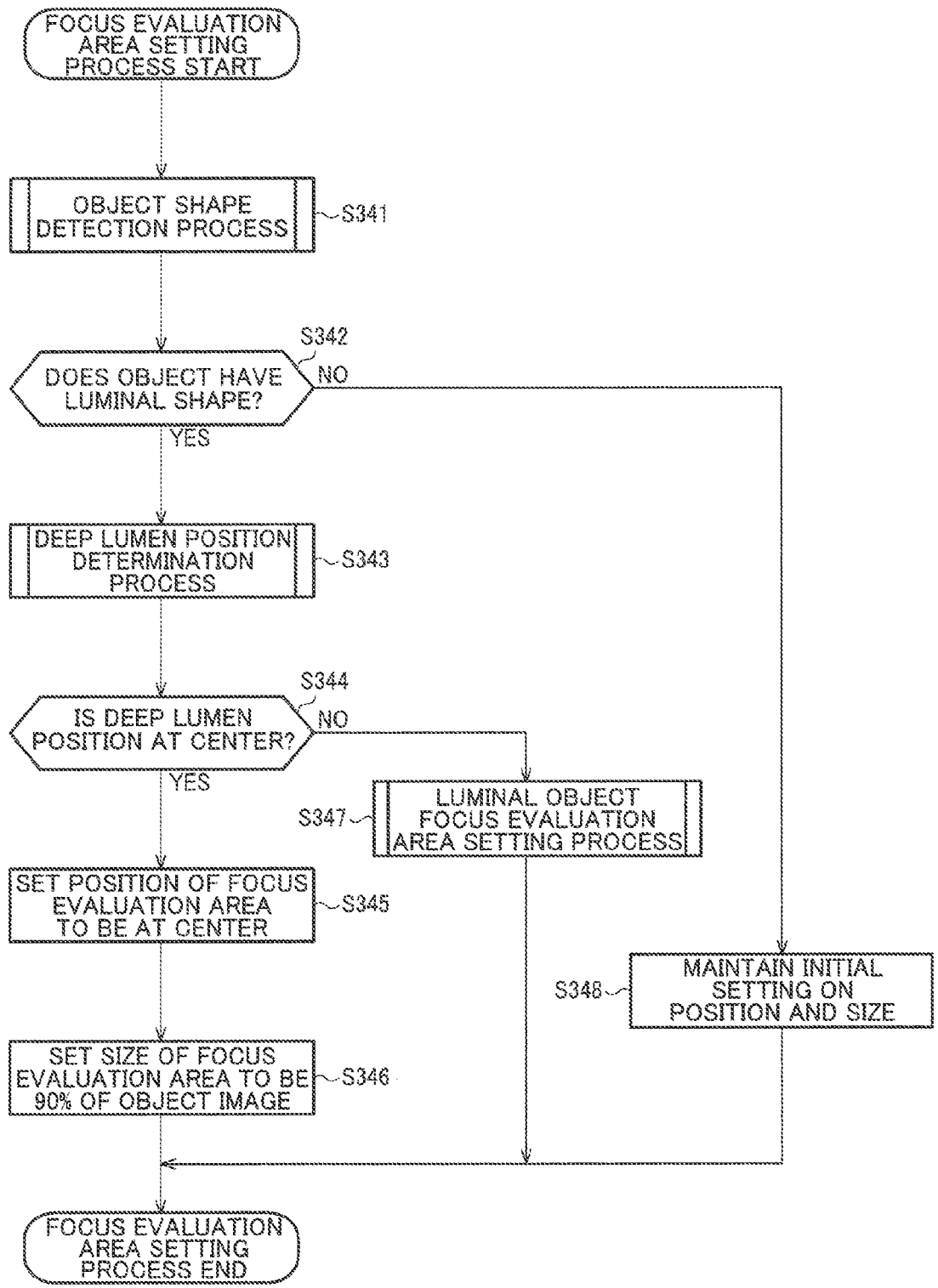
FIG. 6 is a flowchart illustrating a process of setting a focus evaluation area in accordance with an object shape, in a manual focus mode.

FIG. 6 is a flowchart illustrating a process of setting the focus evaluation area in accordance with the object shape, in the MF mode.

First of all, the object shape detection section 315 performs an object shape detection process based on the object image (S341). The object shape detection process is described in detail later. The object shape detection section 315 determines whether or not the object has a luminal shape (S342). When the object has a luminal shape, a deep lumen position determination process is performed (S343). The object shape detection section 315 determines whether or not the deep lumen position is at the center of the object image (S344). When the position is at the center of the object image, the focus evaluation area setting section 340 set the position of the focus evaluation area to be at the center of the object image (S345), and the sets the size of the focus evaluation area to be 90% of the object image in the horizontal direction and in the vertical direction (S346). In step S344, when the deep lumen position is not at the center of the object image, the focus evaluation area setting section 340 performs a luminal subject focus evaluation area setting process to set the position and the size of the focus evaluation area (S347). The luminal subject focus evaluation area setting process is described in detail later. In step S342, when the object does not have a luminal shape, the focus evaluation area setting section 340 maintains the initial setting on the position and the size of the focus evaluation area (S348).

Figure 7:
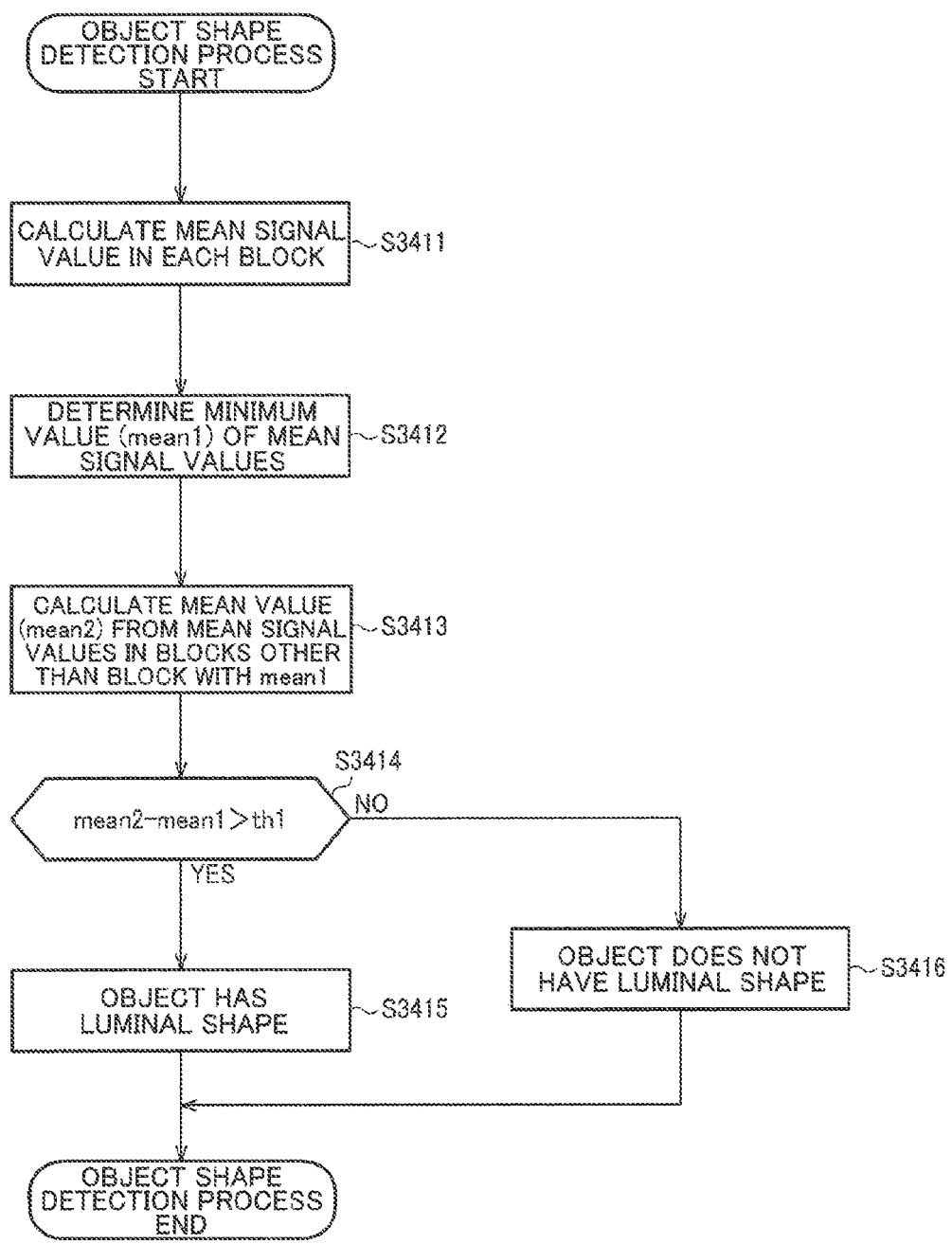
FIG. 7 is a flowchart illustrating an object shape detection process.

FIG. 7 is a flowchart illustrating the object shape detection process.

Figure 8:
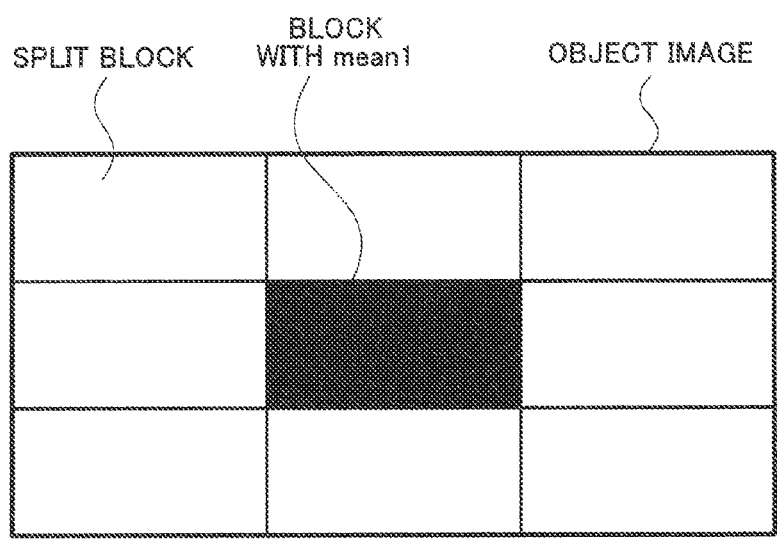
FIG. 8 is a diagram illustrating the object shape detection process.

First of all, the object shape detection section 315 splits the object image into a plurality of split blocks (plurality of split areas) as illustrated in FIG. 8, and calculates a mean signal value in each split block (S3411). In FIG. 8, the object image is split into 3×3 split areas. However, this should not be construed in a limiting sense. The mean signal value is a mean brightness value or the like for example. Next, the object shape detection section 315 determines a minimum value (mean1) of the mean signal values (S3412). Next, the object shape detection section 315 further calculates a mean value (mean2) from the mean signal values in the blocks other than the block with the minimum mean value mean1 (S3413). The object shape detection section 315 compares a difference between the mean value mean2 and the minimum value mean1 with a predetermined threshold (th1) (S3414). The object is detected to have a luminal shape when the difference is larger than the threshold (S3415) and is detected not to have a luminal shape when the difference is not larger than the threshold (S3416).

The deep lumen position determination process (S343) is described. The object shape detection section 315 determines that the deep lumen position is at the center when the block with the minimum value meant determined in the object shape detection process S3412 described above is positioned at the center as illustrated in FIG. 8, and determines that the deep lumen position is not at the center when the block is not positioned at the center.

Figure 9A:
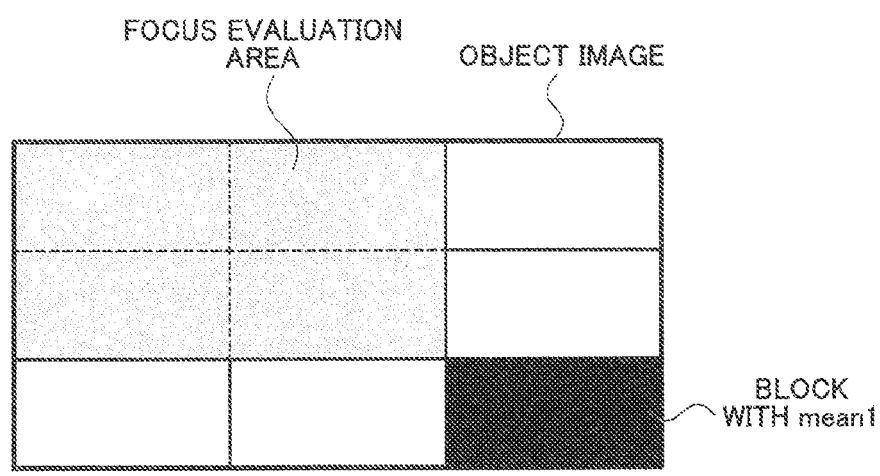
FIG. 9A to FIG. 9C are diagrams illustrating a luminal subject focus evaluation area setting process.
Figure 9B:
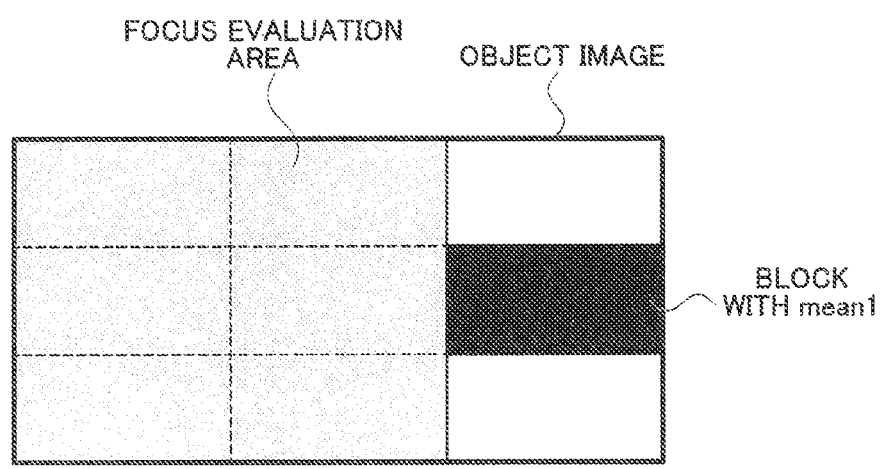
Figure 9C:
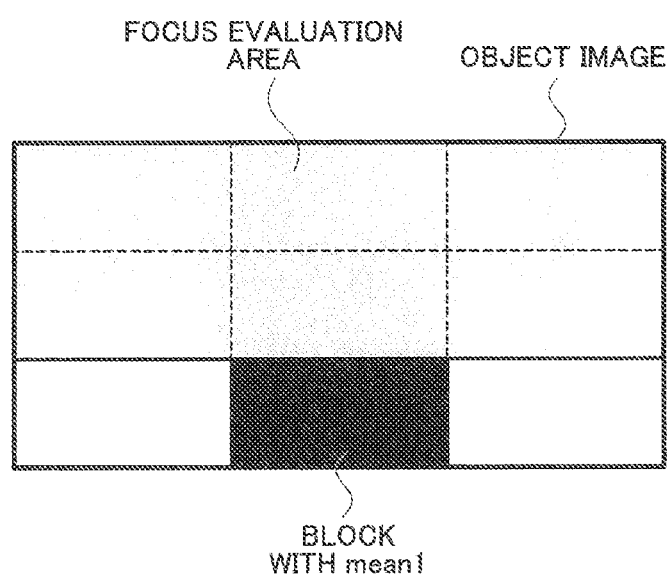

The luminal subject focus evaluation area setting process (S347) is described. As illustrated in FIG. 9A to FIG. 9C, the focus evaluation area setting section 340 sets the focus evaluation area (gray hatched portion) to be symmetrical with respect to the position of the block with the minimum value meant determined in the object shape detection process S3412 described above. The block with the minimum value meant corresponds to the deep lumen position of the luminal subject, and is less likely to include the object desired to be brought into focus by the user. The focus evaluation area illustrated in FIG. 9A to FIG. 9C corresponds to a wall surface of the luminal subject on the near side, and thus is likely to include the object desired to be brought into focus by the user. With the focus evaluation area thus set, the assist information can be displayed for minimum possible areas, whereby a load on the user can be reduced.

For example, the focus evaluation area may be set to be an area at least not including the block with the minimum value meant. Alternatively, the focus evaluation area may be set to be an area including a block (or at least a part of a block) that is point symmetrical to the block with the minimum value meant about the center of the object image.

5. Assist Information and Method for Displaying Assist Information

The assist information generated by the assist information generation section 370 and caused by the image output section 305 to be displayed on the display section 400 is described.

FIG. 10 illustrates an example of the assist information and a method for displaying the assist information. Each of the areas, in the focus evaluation area, determined to be in front focus state or the back focus state is masked with a corresponding color, on the object image. Specifically, only the areas in the front and the back focus states are masked with the object image being somewhat visible through the mask. Preferably, the colors allocated to the front focus area and the back focus area correspond to a front focus operation and a back focus operation by the focus lens operation section 250. For example, when the focus lens operation section 250 includes buttons, a front focus operation button and a back focus operation button are provided with different colors. Thus, the assist information is displayed with a color corresponding to the color of the button. The focus evaluation area (a dotted line frame in FIG. 10) may not be displayed. An area determined to be in focus may or may not be masked.

The assist information and the method for displaying the assist information may be modified in various ways. For example, a first modification may be employed. Specifically, a portion inside each of the front and the back focus areas is colored in FIG. 10. Alternatively, a boundary line (edge) of the area may be colored without coloring the portion inside the area. For example, in FIG. 10, the boundary between the front focus area and the in-focus area, the boundary between the back focus area and the in-focus area, and an outer circumference of the focus evaluation area may be colored with a first color. Thus, the front focus area and the back focus area can each be recognized as an area surrounded by a line with the color.

Furthermore, a second modification illustrated in FIG. 11 may be employed. Specifically, the focus evaluation area may be split into a plurality of partial area, and each of the partial areas is surrounded with a frame line corresponding to the focus status of the area. For example, a partial area determined to be a front focus area is surrounded by a frame line with a first color (a two-dot chained line in FIG. 11) and a partial area determined to be a back focus area is surrounded by a frame line with a second color (a one-dot chained line in FIG. 11). The frame line of the focus evaluation area may or may not be displayed.

6. Scene Detection Section

An operation of the scene detection section 335 and an operation of the assist information generation section 370 based on a result of the scene detection are described with reference to FIG. 12. In the description below, the assist information generation section 370 determines whether or not to generate the assist information based on the scene detection result. However, this should not be construed in a limiting sense. The image output section 305 may determine whether or not to display the assist information based on the scene detection result.

When a treatment involves a large amount of mist generated, or when the object is blurred as a result of a large movement of the rigid scope, the determination for an in-focus, front focus, or back focus state cannot be accurately made. Thus, when such a situation is detected, the assist information is preferably not displayed at all. Specifically, as illustrated in FIG. 12, the scene detection section 335 performs scene detection in each frame of a movie. When the scene detection section 335 detects a predetermined scene (generation of mist), the assist information generation section 370 generates no assist information for a frame with such a detection result and after. When the predetermined scene is no longer detected by the scene detection section 335 thereafter, the assist information generation section 370 resumes generation of the assist information for a frame with such a detection result and after. The scene may be detected by detecting the brightness or saturation or by using a known recognition technique such as motion detection, for example. Furthermore, various modification including generating the assist information when a predetermined scene is detected and generating or not generating the assist information when a predetermined scene change is detected may be employed.

7. Excluded Area Detection Section

An operation of the excluded area detection section 325 and an operation of the assist information generation section 370 based on a result of the excluded area detection are described with reference to FIG. 13. In the description below, the assist information generation section 370 controls the assist information generated area based on a result of the excluded area detection. However, this should not be construed in a limiting sense. The focus evaluation area setting section 340 may control the focus evaluation area based on a result of the excluded area detection or the image output section 305 may control the assist information display area based on a result of the excluded area detection.

An in-focus, front focus, or back focus state cannot be accurately determined for underexposed and overexposed areas. The user would not want such areas to be in focus. Thus, the assist information is preferably not displayed for none of such areas. Specifically, the excluded area detection section 325 compares a pixel value I(x,y) with a threshold th2, and compares the pixel value I(x,y) with a threshold th3. The pixel value I(x,y) is a pixel value of a pixel positioned at coordinates (x,y) of the object image. The threshold th2 is for determining underexposure. The threshold th3 is for determining overexposure. The pixel satisfying the following Formula (1) is detected as the excluded area.

$$I(x,y) < th2 \text{ or } I(x,y) > th3 \quad (1)$$

The excluded area may be provided with display indicating that the area is an excluded area or may not be provided with such display (only the object image may be displayed).

FIG. 14 is a flowchart illustrating the excluded area detection process. First of all, the excluded area detection section 325 selects a pixel in the object image (S3711). Next, the excluded area detection section 325 determines whether or not the selected pixel is within the focus evaluation area (S3712). The process proceeds to step S3713 when the pixel is within the focus evaluation area, and proceeds to step S3715 when the pixel is outside the focus evaluation area. In step S3713, the excluded area detection section 325 determines that the pixel selected in step S3711 is a pixel in the excluded area when the pixel value I(x,y) of the pixel satisfies Formula (1) described above (S3714). The process proceeds to step S3715 when the pixel value I(x,y) does not satisfy Formula (1). The excluded area detection section 325 determines whether or not the process described above has been performed for all the pixels (S3715). When all the pixels have been processed, the excluded area detection is terminated. The process returns to step S3711, when not all the pixels have been processed.

8. Modification of Assist Information and Method for Displaying Assist Information FIG. 15 illustrates a third modification of the assist information and the method for displaying the assist information.

The assist information displayed to be overlapped with the object image might compromise the visibility of the object. Thus, the object image is displayed in a first area, and the assist information is sub-displayed in a second area different from the first area. This sub displaying is enabled only in the MF mode. In the second area, the assist information may only be displayed without being overlapped with the object image, or the image with the assist information overlapped with the object image may be displayed.

FIG. 16 illustrates a fourth modification of the assist information and the method for displaying the assist information.

The assist information distant from the object image leads to a large movement of a viewpoint of the user, resulting in fatigue. Thus, the assist information is displayed in the object image in a Picture in Picture (PiP) manner. Specifically, the object image is displayed in a first area, and the assist information is displayed in a second area inside the first area. This sub display is enabled only in the MF mode. The first area may be the same as or different from the display area of the display section 400.

The embodiments and the modifications thereof according to the present invention are described. However, the present invention is not limited the embodiments and the modifications only, and the present invention can be implemented with the elements modified without departing from the gist of the invention. The plurality of elements disclosed in the embodiments and the modifications may be combined as appropriate to implement the invention in various ways. For example, some of all the elements described in the embodiments and the modifications may be deleted. Furthermore, elements in different embodiments and modifications may be combined as appropriate. Thus, various modification and application can be made without departing from the gist of the present invention. Any term cited with a different term having a broader meaning or the same meaning at least once in the specification and the drawings can be replaced by the different term in any place in the specification and the drawings.

What is claimed is:

1. An imaging device comprising a processor, wherein the processor is configured to:
set a focus evaluation area in an object image obtained by an imaging section including an optical system in which an in-focus object plane position is changeable,
control the in-focus object plane position based on operation input information in a manual focus mode, and control the in-focus object plane position based on a focus evaluation value obtained from an image of the focus evaluation area in an auto focus mode,
output the object image to a display section, and
detect an object shape from the object image,
wherein the processor is configured to implement, in the manual focus mode, setting the focus evaluation area such that a ratio of the focus evaluation area to the object image is greater than the ratio in the auto focus mode,
obtaining the focus evaluation value from an image of the set focus evaluation area,
generating assist information assisting adjustment of the in-focus object plane position based on the obtained focus evaluation value, and
outputting the assist information on an area, in the object image, for which at least one of a position, a size, and a shape is controlled based on the object shape detected from the object image, to the display section.

2. The imaging device as defined in claim 1, wherein the processor is configured to set the focus evaluation area satisfying at least one of MH>LH×50% and MV>LV×50% in the manual focus mode, where LH represents a size of the object image in a horizontal scanning direction, LV represents a size of the object image in a vertical scanning direction, MH represents a size of the focus evaluation area in the horizontal scanning direction, and MV represents a size of the focus evaluation area in the vertical scanning direction.

3. The imaging device as defined in claim 1,
wherein the processor is configured to set the focus evaluation area to have a center positioned at a center of the object image, in the manual focus mode.

4. An endoscope apparatus comprising the imaging device as defined in claim 1.

5. A method for operating an imaging device, the method comprising:
- in a manual focus mode in which an in-focus object plane position of an imaging section is controlled based on operation input information, setting a focus evaluation area such that a ratio of the focus evaluation area to the object image is greater than the ratio in an auto focus mode in which the in-focus object plane position is controlled based on a focus evaluation value, to an object image obtained by the imaging section;
- obtaining the focus evaluation value from an image of the set focus evaluation area, generating assist information assisting adjustment of the in-focus object plane position based on the obtained focus evaluation value;
- detecting an object shape from the object image; and
- outputting the assist information on an area, in the object image, for which at least one of a position, a size, and a shape is controlled based on the object shape detected from the object image, and the object image to the display section, in the manual focus mode.

* * * * *